United States Patent
Katz et al.

(10) Patent No.: US 11,915,416 B2
(45) Date of Patent: Feb. 27, 2024

(54) MULTI-LAYERED VISUALIZATION OF DATA POINTS OVER HEART MAP

(71) Applicant: BIOSENSE WEBSTER (ISRAEL) LTD., Yokneam (IL)

(72) Inventors: Natan Sharon Katz, Atlit (IL); Benjamin Cohen, Haifa (IL); Vladimir Dvorkin, Kiryat Motzkin (IL); Lior Zar, Poria Illit (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 485 days.

(21) Appl. No.: 17/234,871

(22) Filed: Apr. 20, 2021

(65) Prior Publication Data
US 2022/0335598 A1    Oct. 20, 2022

(51) Int. Cl.
*G06T 7/12* (2017.01)
*G06T 7/00* (2017.01)
*G16H 30/40* (2018.01)
*A61B 5/00* (2006.01)

(52) U.S. Cl.
CPC ............ *G06T 7/0012* (2013.01); *A61B 5/743* (2013.01); *G16H 30/40* (2018.01); *G06T 2207/30048* (2013.01)

(58) Field of Classification Search
CPC ......... G06T 7/0012; G06T 2207/30048; A61B 5/743; A61B 5/367; A61B 5/339; A61B 5/7264; A61B 5/7435; A61B 5/0036; A61B 5/0044; A61B 5/349; A61B 18/00; A61B 2018/00351; A61B 2018/00577; A61B 2018/00589; A61B 2018/00839; G16H 30/40

USPC .......................................................... 382/128
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |

(Continued)

FOREIGN PATENT DOCUMENTS

| | | |
|---|---|---|
| EP | 2638853 A1 | 9/2013 |
| WO | 199605768 A1 | 2/1996 |

(Continued)

OTHER PUBLICATIONS

European Search Report for corresponding EPA No. 22168786.6 dated Sep. 15, 2022.

*Primary Examiner* — Charlotte M Baker (57) ABSTRACT

A system includes a display and a processor. The processor is configured to: (i) receive a dataset including multiple data points, each data point corresponding to one or more properties of an organ of a patient, (ii) produce, based on a clustering criterion, at least a cluster including two or more of the data points, and (iii) produce and present on the display, a map of the organ and at least an object indicative of the cluster. In response to selection of the object by a user, the processor is configured to produce and present on the display, a two-dimensional (2D) table including the one or more properties of each of the clustered data points.

14 Claims, 3 Drawing Sheets

(56) References Cited

U.S. PATENT DOCUMENTS

| | | |
|---|---|---|
| 10,709,347 B1 | 7/2020 | Villongco |
| 2002/0065455 A1 | 5/2002 | Ben-Haim et al. |
| 2003/0120150 A1 | 6/2003 | Govari |
| 2004/0068178 A1 | 4/2004 | Govari |
| 2014/0058282 A1* | 2/2014 | O'Grady .............. A61B 5/6852 600/546 |
| 2016/0292847 A1* | 10/2016 | Liu ........................... G06T 7/10 |
| 2017/0035320 A1* | 2/2017 | Verma .................. A61B 5/0042 |
| 2018/0279895 A1* | 10/2018 | Relan ..................... G06T 11/206 |
| 2018/0279896 A1 | 10/2018 | Ruppersberg |
| 2019/0192039 A1* | 6/2019 | Wang ................... A61B 5/4064 |
| 2019/0333639 A1 | 10/2019 | Villongco |
| 2021/0165852 A1* | 6/2021 | Granger ................ G06V 10/82 |
| 2021/0386355 A1* | 12/2021 | Ravuna ................ A61B 5/7267 |

FOREIGN PATENT DOCUMENTS

| | | |
|---|---|---|
| WO | WO2011080385 A1 | 7/2011 |
| WO | WO2015148470 A1 | 10/2015 |
| WO | 2017125114 A1 | 7/2017 |

* cited by examiner

MULTI-LAYERED VISUALIZATION OF DATA POINTS OVER HEART MAP

FIELD OF THE INVENTION

The present invention relates generally to medical devices, and particularly to methods and systems for multi-layered visualization of data points over a heart map.

BACKGROUND OF THE INVENTION

Various techniques for visualizing information, such as electrophysiological data, on anatomical maps have been published.

For example, U.S. Patent Application Publication No. 2018/0279896 describes a system for analyzing electrophysiological data, especially intracardial electrogram data. The system comprising a data processing and control unit for processing the electrophysiological data, a data output unit comprising a data output screen for displaying results of electrophysiological data analysis. The data processing and control unit being configured to receive electrophysiological data obtained from a mapping catheter assembly that comprises an electrode assembly with a plurality of n electrodes, each electrode configured for measuring electrophysiological data in the form of electrogram signals. The data processing and control unit comprises an engine for performing an optical flow analysis of the electrophysiological data to generate series of vector data representing the average speed and direction of movement of clusters of the electrophysiological data. The data output unit being configured to display the vector data on a data output screen of the data output unit.

U.S. Pat. No. 10,709,347 describes a system for displaying heart graphic information relating to sources and source locations of a heart disorder to assist in evaluation of the heart disorder. A heart graphic display system provides an intra-cardiogram similarity ("ICS") graphic and a source location ("SL") graphic. The ICS graphic includes a grid with the x-axis and y-axis representing patient cycles of a patient cardiogram with the intersections of the patient cycle identifiers indicating similarity between the patient cycles. The SL graphic provides a representation of a heart with source locations indicated. The source locations are identified based on similarity of a patient cycle to library cycles of a library cardiogram of a library of cardiograms.

SUMMARY OF THE INVENTION

An embodiment of the present invention that is described herein provides a system, including a display and a processor. The processor is configured to: (i) receive a dataset including multiple data points, each data point corresponding to one or more properties of an organ of a patient, (ii) produce, based on a clustering criterion, at least a cluster including two or more of the data points, and (iii) produce and present on the display, a map of the organ and at least an object indicative of the cluster. In response to selection of the object by a user, the processor is configured to produce and present on the display, a two-dimensional (2D) table including the one or more properties of each of the clustered data points.

In some embodiments, the organ includes a patient heart, and the clustering criterion is selected from a list of criteria consisting of: (i) a location of the data point in the heart, (ii) a morphology of a signal acquired at the data point, (iii) a local activation time (LAT) measured at the data point, and (iv) an anatomical feature at the data point. In other embodiments, the processor is configured to present at least the object by displaying the object over the map.

In an embodiment, the processor is configured to produce and present at least the object by displaying the object in an additional 2D table. In another embodiment, the processor is configured to assign to the cluster a representative data value, which represents a calculated value corresponding to the clustered data points.

There is additionally provided, in accordance with an embodiment of the present invention, a method including receiving a dataset including multiple data points, each data point corresponding to one or more properties of an organ of a patient. At least a cluster that includes two or more of the data points is produced based on a clustering criterion. A map of the organ and at least an object indicative of the cluster are produced and presented, and in response to selection of the object by a user, a two-dimensional (2D) table that includes the one or more properties of each of the clustered data points, is produced and displayed.

There is further provided, in accordance with an embodiment of the present invention, a method for multi-layered visualization, the method includes receiving a dataset including multiple data points, each data point corresponding to one or more properties of an organ of a patient. A first visualization layer is produced by clustering, based on a clustering criterion, at least a cluster including two or more of the data points, and an object indicative of the cluster is displayed. A second visualization layer that includes a two-dimensional (2D) table having the one or more properties of each of the clustered data points, is produced, and the 2D table is displayed in response to selection of the object by a user.

In some embodiments, producing the first visualization layer includes displaying the object over the map. In other embodiments, producing the first visualization layer includes displaying the object in an additional 2D table. In yet other embodiments, producing the first visualization layer includes assigning to the object a representative data value that represents a calculated value corresponding to the clustered data points.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Some medical procedures, such as cardiac radiofrequency (RF) ablation, require electro-anatomical mapping of the heart before performing the ablation. In the mapping, a physician inserts a catheter having multiple sensing electrodes, each electrode configured to produce one or more signals indicative of electro-physiological (EP) signals sensed in tissue of the patient heart.

The signals produced by the sensing electrodes of the catheter may comprise thousands of data points, for example, about 50,000 data points or even more. Based on the data points, the physician may determine a plan for ablating tissue in the heart. However, the large number of data points may confuse the physician and may interfere with the setting of the ablation plan.

Embodiments of the present invention that are described hereinbelow provide improved techniques for presenting large amount (e.g., hundreds or thousands) of data points indicative of one or more properties of a patient organ, such as a patient heart.

In some embodiments, a system for presenting the data points comprises a display and a processor. The processor is configured to receive a dataset comprising the plurality of data points, each data point corresponding to one or more properties of the patient heart.

In some embodiments, the processor is configured to produce, based on one or more clustering criteria, at least a cluster (and typically multiple clusters) comprising a plurality of the data points. The processor is further configured to produce and present on the display, an anatomical map of the heart and multiple objects indicative of the multiple clusters, respectively.

In principle, clustering the data points simplifies the visualization of the data points over the anatomical map, and therefore, may help the physician in determining the ablation plan. In some cases, however, the clustering may conceal or overlook one or more data points having values of properties that may affect the ablation plan.

In some embodiments, the processor is configured to assign to each cluster a representative data value, which represents a calculated value corresponding to the clustered data points. For example, an average and a standard deviation of the values of a property selected for the ablation criterion, which are calculated for all the data points clustered in the respective cluster. In some embodiments, the physician may view the data values by hovering with a trackball or a mouse of the system, over the clusters displayed over the anatomical map of the heart. Additionally or alternatively, the physician may use any other suitable technique, such as viewing the data values of each cluster in a table having some or all of the clusters.

In some embodiments, the processor is configured to analyze the data values of the clusters and provide the physician with an alert in case one or more of the data values exceed a predefined threshold.

In some cases the data value(s) of a given cluster may draw the attention of the physician. For example, in case the standard deviation is larger than a predefined threshold. In such cases, the physician may select the given cluster, for example, by clicking on the object, which is displayed over the anatomical map and is indicative of the given cluster.

In some embodiments, in response to a selection of the object by the physician (or by any other user of the system), the processor is configured to produce and present on the display, a two-dimensional (2D) table comprising the properties of each of the data points clustered in the given cluster.

The disclosed techniques provide the physician with a multi-layered visualization of data points indicative of properties of a patient organ. The processor is configured to produce a first visualization layer by clustering, based on a clustering criterion, at least a cluster comprising two or more of the data points, and to display the object indicative of the cluster, on the anatomical map. The processor is further configured to produce a 2D table having the one or more properties of each of the clustered data points. Moreover, in response to a selection of the object by the user (e.g., the physician), the processor is configured to display the 2D table on the display (i.e., the 2D table constitutes a second visualization layer), so that the physician can review the properties of one or more data points clustered within the given cluster.

The disclosed techniques may help physicians in collecting and analyzing diagnostic data for determining various types of treatment procedures, such as but not limited to cardiac RF ablation. Specifically, by providing the physician with a multi-layered visualization and displaying of the properties associated with the organ in question, the disclosed techniques simplify the diagnostics and planning, but provide the user (e.g., the physician) with the capability to review one or more specific data points, which may be essential for appropriate determination of the treatment plan.

System Description

Figure 1:
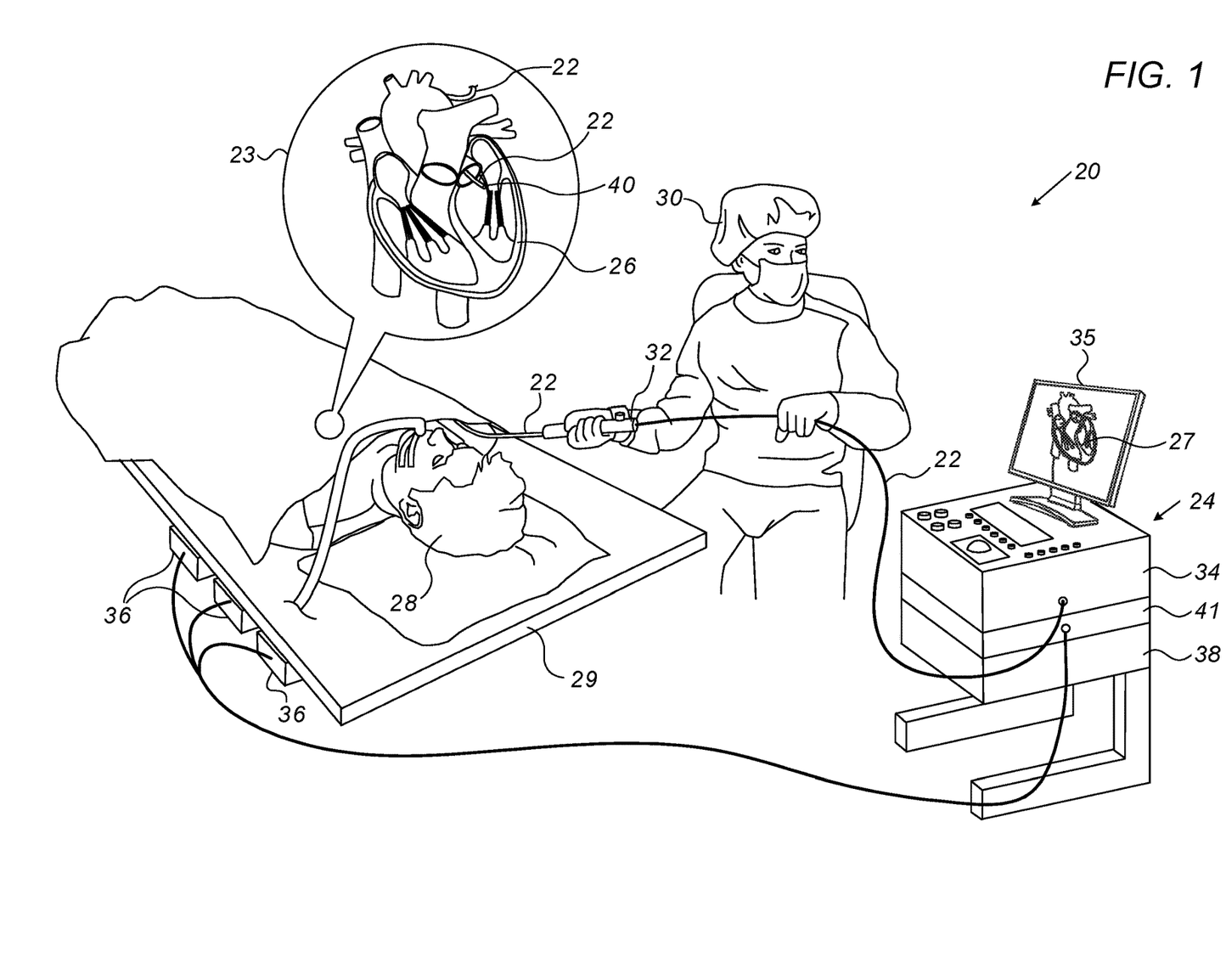
FIG. 1 is a schematic, pictorial illustration of a catheter-based tracking and ablation system, in accordance with an exemplary embodiment of the present invention.

FIG. 1 is a schematic, pictorial illustration of a catheter-based tracking and ablation system 20, in accordance with an embodiment of the present invention.

In some embodiments, system 20 comprises a catheter 22, in the present example a cardiac catheter, and a control console 24. In the embodiment described herein, catheter 22 may be used for any suitable therapeutic and/or diagnostic purposes, such as ablation of tissue in a heart 26.

In some embodiments, console 24 comprises a processor 41, typically a general-purpose computer, with suitable front end and interface circuits 38 for receiving signals via catheter 22 and for controlling the other components of system 20 described herein. Console 24 further comprises a user display 35, which is configured to receive from processor 41 a map 27 of heart 26, and to display map 27.

In some embodiments, map 27 may comprise any suitable type of anatomical map produced using any suitable technique. For example, the anatomical map may be produced using an anatomical image produced by using a suitable medical imaging system, or using a fast anatomical mapping (FAM) techniques using the CARTO™ system, produced by Biosense Webster Inc. (Irvine, Calif.), or using any other suitable technique, or using any suitable combination of the above.

Reference is now made to an inset 23. In some embodiments, prior to performing an ablation procedure, a physician 30 inserts catheter 22 through the vasculature system of a patient 28 lying on a table 29, so as to perform electro-anatomical mapping of tissue in question of heart 26.

In some embodiments, catheter 22 comprises a distal-end assembly 40 having multiple sensing electrodes (not shown). For example, distal-end assembly 40 may comprise: (i) a basket catheter having multiple splines, each spline having multiple sensing electrodes, or (ii) a balloon catheter having multiple sensing electrodes disposed on the surface of the balloon. Each sensing electrode is configured to produce, in response to sensing electrophysiological (EP) signals in tissue of heart 26, one or more signals indicative of the sensed EP signals.

In some embodiments, the proximal end of catheter 22 is connected, inter alia, to interface circuits 38, so as to transfer these signals to processor 41 for performing the electro-anatomical mapping.

In some embodiments, during the electro-anatomical mapping, the signals produced by the sensing electrodes of distal-end assembly 40 may comprise thousands of data points, for example, about 50,000 data points or more. Based on the data points, physician 30 determines one or more sites for ablating tissue in heart 26. However, physician 30 may have difficulties to review and analyze the aforementioned large number of data points, which may prolong the duration of the ablation procedure. Moreover, the large amount of data points may confuse physician 30, which may reduce the quality of the ablation planning.

In the context of the present disclosure and in the claims, the terms "about" or "approximately" for any numerical values or ranges indicate a suitable dimensional tolerance that allows the part or collection of components to function for its intended purpose as described herein.

In some embodiments, processor 41 is configured to present the data points, e.g., on display 35, in two visualization layers by: (i) clustering data points, based on one or more clustering criteria, and displaying an object indicative of each cluster, and (ii) in response to selection of the object by physician 30 (or by any other user of system 20), display a two-dimensional (2D) table comprising the properties of each of the clustered data points.

In some embodiments, displaying in two visualization layers can: (i) simplify the presentation of thousands of data points to physician 30, by displaying the data points in clusters (e.g., on map 27), and (ii) allow physician 30 to examine specific data points within each selected cluster. The techniques for displaying in two visualization layers are described in detail in FIG. 2 below.

In some embodiments, physician 30 may use processor 41 for clustering the data points into multiple clusters, so that physician 30 may review and analyze the clusters constituting smaller amount of data. However, some of the clustered data points may be essential for appropriate determination of the ablation plan. Therefore, presenting the data points in clusters may not be sufficient for producing the most clinically suitable ablation plan.

In some embodiments, processor 41 is configured to present the data points in two or more levels so as to: (i) reduce the amount of data (e.g., by clustering) for simplifying the data analysis, and yet, (ii) provide physician 30 with the capability to review one or more specific data points (e.g., within the clusters).

In some embodiments, processor 41 is configured to receive a dataset comprising multiple data points. Each data point corresponding to one or more properties of heart 26. Processor 41 is configured to produce, based on a clustering criterion, multiple clusters, so that at least one of the clusters comprises two or more (typically tens or hundreds) of the data points. Processor 41 is further configured to assign to each cluster a representative data value, which represents a calculated value corresponding to the clustered data points.

In some embodiments, processor 41 is configured to produce map 27 of heart 26 comprising the one or more clusters, and to display objects indicative of the respective clusters, over map 27 displayed on display 35. Additionally or alternatively, processor 41 is configured to display the clusters in a two-dimensional (2D) table, e.g., adjacent to the anatomical map. The clustering reduces the amount of data points to be analyzed by physician 30, as described above.

In some embodiments, physician 30 may select a cluster for reviewing one or more properties associated with a specific data point within the cluster. In such embodiments, in response to selecting an object indicative of a respective cluster, processor 41 is configured to produce a 2D table comprising one or more properties of each of the clustered data points, and to display, on display 35, the 2D table. These techniques are depicted in detail in FIGS. 2 and 3 below.

In other embodiments, catheter 22 may comprise one or more ablation electrodes (not shown) coupled to distal-end assembly 40. The ablation electrodes are configured to ablate tissue at a target location of heart 26. After determining the ablation plan, physician 30 navigates distal-end assembly 40 in close proximity to the target location in heart 26 by using a manipulator 32 for manipulating catheter 22. Additionally or alternatively, physician 30 may use any different sort of suitable catheter for ablating tissue of heart 26 so as to carry out the aforementioned ablation plan.

In some embodiments, the position of distal-end assembly 40 in the heart cavity is measured using a position sensor (not shown) of a magnetic position tracking system. In the present example, console 24 comprises a driver circuit 34, which is configured to drive magnetic field generators 36 placed at known positions external to patient 28 lying on table 29, e.g., below the patient's torso. The position sensor is coupled to the distal end, and is configured to generate position signals in response to sensed external magnetic fields from field generators 36. The position signals are indicative of the position the distal end of catheter 22 in the coordinate system of the position tracking system.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

In some embodiments, the coordinate system of the position tracking system are registered with the coordinate systems of system 20 and map 27, so that processor 41 is configured to display on map 27, the position of the distal end of catheter 22.

In some embodiments, processor 41, typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of medical systems.

Two-Level Visualization of Data Points Over Heart Map

Figure 2:
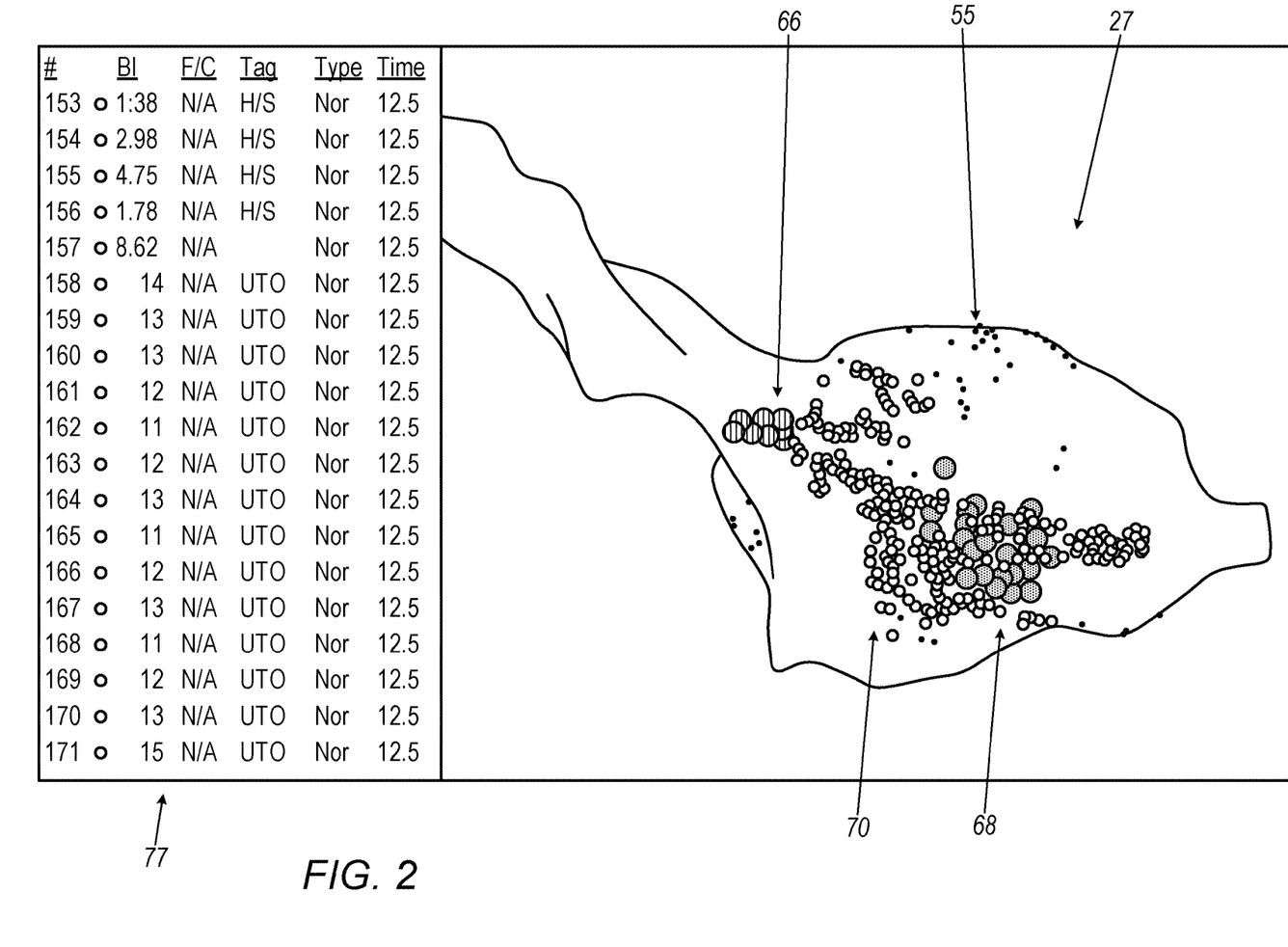
FIG. 2 is a schematic, pictorial illustration of multi-layered visualization of data points presented in clusters and in a two-dimensional table of a selected cluster, in accordance with an exemplary embodiment of the present invention.

FIG. 2 is a schematic, pictorial illustration of map 27 and a multi-layered visualization of data points 55 displayed on display 35, in accordance with an embodiment of the present invention.

In some embodiments, processor 41 is configured to receive from distal-end assembly 40 the signals described in FIG. 1 above. The signals comprise a dataset comprising multiple data points 55. Each data point corresponding to one or more properties of heart 26. Processor 41 is configured to produce, based on a clustering criterion, multiple clusters, so that at least one of the clusters comprises two or more (typically tens or hundreds or thousands) of data points 55. In the present example, processor 41 is configured to produce and present clusters 66 and 68, and optionally, data points 55 (which are not clustered), over map 27 that is displayed on display 35.

In some embodiments, processor 41 is configured to present, on display 35, clusters 66, 68 and 70, and data points 55 using any suitable objects. In the present example, data points 55 may be presented using round-shaped objects having a given color (e.g., orange) and a given diameter, one or more clusters 66 may be presented using round-shaped objects having a yellow color and one or more different diameters, one or more clusters 68 may be presented using round-shaped objects having a red color and one or more different diameters, and clusters 70 may be presented using round-shaped objects having a green color and one or more different diameters.

In other embodiments, the objects indicative of the clusters may have any suitable shape other than round, e.g., an ellipse or any sort of an irregular shape.

In some embodiments, processor 41 is configured to assign the diameter of the round-shaped object to be indicative of the number of data points 55 clustered in the object. In other embodiments, the diameter of the round-shaped object may be indicative of the area covered by the clustered data points 55. In the present example, the objects indicative of clusters 66 and 68 typically have a larger diameter than the objects indicative of clusters 70. Similarly, the objects indicative of clusters 70 have a diameter larger than the objects indicative of data points 55.

In some embodiments, processor 41 is configured to apply multiple different clustering criteria for clustering data points 55 at different sections of map 27, and to assign a different color or a different shape for presenting every property and/or clustering criterion over map 27.

In some embodiments, the clustering criterion may be based on one or more properties of heart 26, or based on properties of any other organ in question. In the present example, processor 41 is configured to select the clustering criterion from a list of criteria consisting of: (i) the location of data points 55 on map 27 of heart 26, (ii) the morphology of the EP signal acquired by the electrodes of distal-end assembly 40 at the positions of data points 55, (iii) the local activation time (LAT) measured by the electrodes of distal-end assembly 40 at the positions of data points 55, (iv) the anatomical feature of heart 26 at each data point 55, or any other suitable property and/or clustering criterion.

In some embodiments, processor 41 is further configured to assign to each cluster a representative data value, which represents a calculated value corresponding to the clustered data points 55. For example, console 24 may comprise an input device, such as a trackball or a mouse, and when physician 30 hovers with the input device over cluster 66, processor 41 is configured to present on display 35, the calculated value corresponding to the respective cluster 66.

In some embodiments, the calculated value may comprise, for example, an average and a standard deviation of the parameter selected for the clustering criterion, which are calculated by processor 41 for the clustered data points 55 of the selected cluster 66. Additionally or alternatively, the calculated value may comprise any other statistical calculation and/or other properties, such as the minimal or maximal or average distance between adjacent clustered data points 55 of the selected cluster 66.

In other embodiments, instead of or in addition to the objects displayed over map 27, processor 41 is configured to present at least some of clusters 66, 68 and 70, and/or at least some of data points 55, using a two-dimensional (2D) table (not shown), also referred to herein as "a clusters table" or "an additional table." In such embodiments, each line of the table constitutes an object indicative of the respective cluster. The line of the table may comprise, in the columns of the 2D table, some or all of the calculated values of the cluster in question, using the techniques and embodiments described above for the rounded-shaped objects displayed over map 27.

In some cases, physician 30 may wish to review one or more data points 55 of a given cluster. For example, in case the standard deviation of the LAT of one cluster 66 is higher than a predefined threshold.

In some embodiments, processor 41 is configured to present a 2D table 77 of a selected cluster, so that physician 30 can review the properties associated with each data point 55 of the respective cluster. In the example of FIG. 2, physician 30 (or any other user) may select an object indicative of a cluster 66, e.g., by clicking on the object presented over map 27.

In some embodiments, in response to the object selection by physician 30, processor 41 is configured to produce and display, on display 35, table 77 having all the selected properties (e.g., measured and/or calculated) of each data point 55 clustered in the selected cluster 66.

In some embodiments, table 77 may comprise the shape and color of the object assigned to each data point 55 of table 55. In the present example, a yellow round shape, wherein each data point may have a gradient indicative of a value of a property selected for the clustering, or any other selected property. In response to a user selection, processor 41 is configured to allow the user to browse, read, filter, sort or manipulate the properties of data points 55 displayed in table 77.

In some embodiments, in response to an instruction from the user (e.g., physician 30) processor 41 is configured to remove table 77 from display 35, or alternatively, to display multiple tables 77, each of which indicative of the different cluster selected from among clusters 66, 68 and 70, as well as selected data points 55 that are not clustered.

In other embodiments, processor 41 is configured to display table 77 in response to a selection of the aforementioned cluster 66 from the clusters table having at least some of the clusters, as described above.

This particular presentation of map 27, the clusters, data points 55, and table 77 of FIG. 2, is shown by way of example, in order to illustrate certain problems that are addressed by embodiments of the present invention and to demonstrate the application of these embodiments in enhancing the performance of system 20, and improving the quality and cycle time of the data analysis and ablation planning. Embodiments of the present invention, however, are by no means limited to this specific sort of example presentation, and the principles described herein may similarly be applied to other sorts of user interfaces applied to any other suitable medical procedures carried out using any suitable medical systems.

Figure 3:
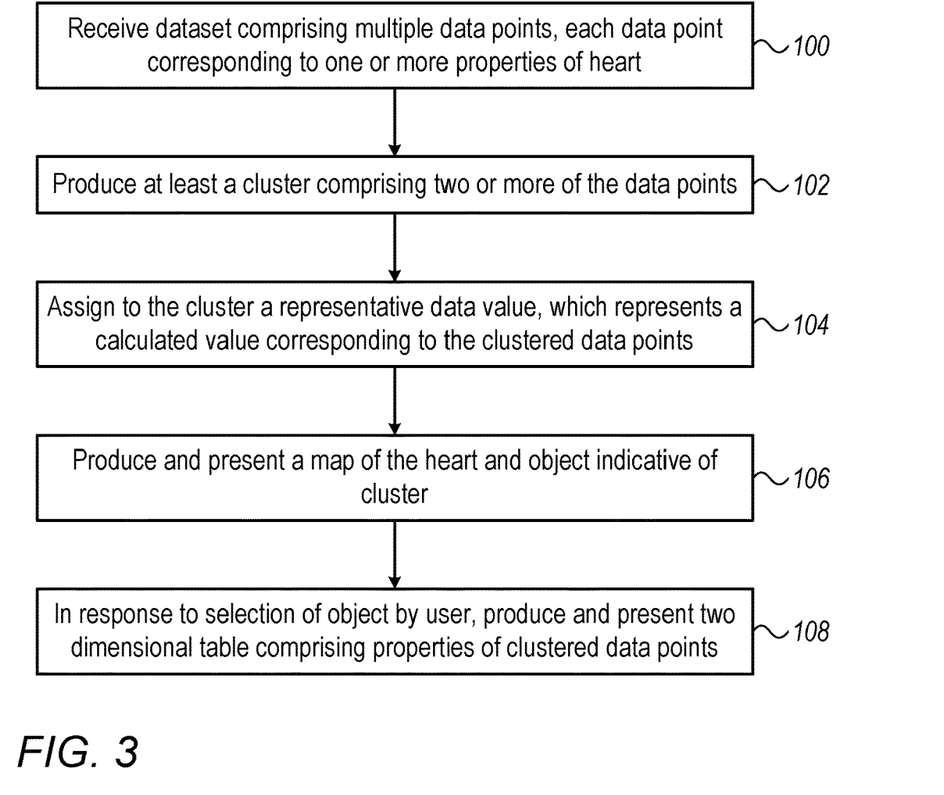
FIGS. 3 and 4 are flow charts that schematically illustrate methods for visualizing data points over a heart map, in accordance with exemplary embodiments of the present invention.

FIG. 3 is a flow chart that schematically illustrates a method for a two-level visualization of data points 55 over map 27, in accordance with an embodiment of the present invention. In the context of the present disclosure and in the claims, the terms "two-level," "multi-level," "two layers" and "multi-layered" are used interchangeably and refer to presenting any sort of data in multiple layers by providing the user with the capability to select the layer or level of information he or she wants to view.

The method begins at a dataset receiving step 100, with processor 41 or any other device that receives from distal-end assembly 40, a dataset comprising multiple data points 55. Each data point corresponding to one or more properties of heart 26. At a cluster production step 102, processor 41 is configured to produce, based on a clustering criterion (or based on multiple clustering criteria), at least cluster 66 comprising two or more of data points 55. As shown in the example of FIG. 2, processor 41 is configured to produce multiple clusters 66, 68 and 70, each of which has multiple (e.g., hundreds or thousands of) data points 55.

At a representative data value assignment step 104, processor 41 is configured to assign to the cluster (e.g., cluster 66) a representative data value, which represents a calculated value corresponding to data points 55 that are clustered within cluster 66, as described in detail in FIG. 2 above.

At a map and cluster presentation step 106, processor 41 is configured to produce and present map 27 of heart 26, and one or more objects indicative of one or more clusters, such as clusters 66, 68 and 70, as described in detail in FIG. 2 above.

At a table presentation step 108 that concludes the method, in response to the selection (by physician 30 or any other user) of the aforementioned one or more objects, e.g., the object indicative of one cluster 66, processor 41 is configured to produce and present (e.g., on display 35) two-dimensional (2D) table 77 comprising properties of data points 55 clustered in selected cluster 66.

As described in detail in FIG. 2 above, in step 106, the objects indicative of the clustered data points may be displayed on display 35 using any other suitable presentation, for example, in an additional 2D table.

Figure 4:
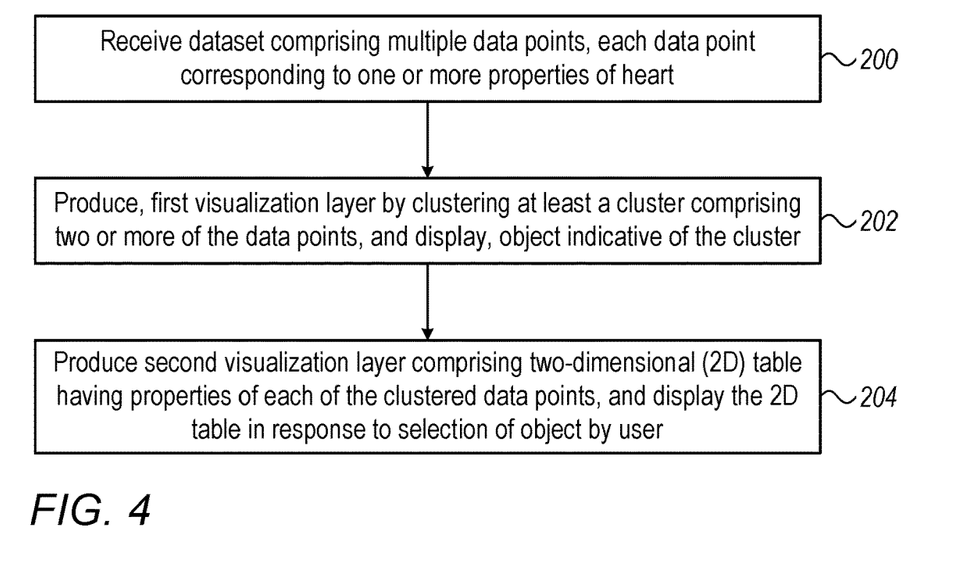

FIG. 4 is a flow chart that schematically illustrates a method for a two-level visualization of thousands of data points 55, in accordance with another embodiment of the present invention.

The method begins at a dataset receiving step 200 with processor 41 receiving from distal-end assembly 40, a dataset comprising multiple data points 55, each data point corresponding to one or more properties of heart 26.

At a first visualization layer production step 202, processor 41 is configured to produce a first visualization layer by clustering, based on a clustering criterion, at least cluster 66 (and typically additional clusters, such as clusters 68 and 70) comprising two or more of data points 55. Processor is further configured to display one or more objects indicative of one or more clusters (e.g., clusters 66, 68 and 70), respectively, as shown and described in detail in FIG. 2 above.

In some embodiments, processor 41 is further configured to assign to the cluster (e.g., cluster 66) a representative data value, which represents a calculated value corresponding to data points 55 that are clustered within cluster 66, as described in detail in FIG. 2 above and also in step 104 of FIG. 3 above. Moreover, in addition to or instead of the visual objects presented over map 27, processor 41 is configured to present one or more of clusters 66, 68 and 70, and optionally at least some of data points 55, in an additional table, also referred to as the cluster table described in FIG. 2 above.

At a second visualization layer production step 204 that concludes the method, processor 41 is configured to produce a second visualization layer. In the present example, the second visualization layer comprises 2D table 77 (shown in FIG. 2 above) having properties of each of the clustered data points 55. In some embodiments, in response to selection of the object indicative of cluster 66 by physician 30 (or by any other user) processor 41 is configured to display table 77 on display 35, as described in detail in FIG. 2 above.

Although the embodiments described herein mainly address visualization of electrophysiological (EP) data points on a cardiac anatomical map, the methods and systems described herein can also be used in other applications, such as in mapping and visualizing of any properties of any organ of a patient. Moreover, the embodiments described herein can be used in presenting any sort of large amount (e.g., thousands or millions) of data, such that the data is clustered using one or more clustering criteria, each cluster is characterized with annotations, and the data within each cluster can be presented using any suitable format.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a display; and
a processor, which is configured to: (i) receive a dataset comprising multiple data points, each data point corresponding to one or more properties of an organ of a patient, (ii) produce, based on a clustering criterion, at least a cluster comprising two or more of the data points, and (iii) produce and present on the display, a map of the organ and at least an object indicative of the cluster, and
in response to selection of the object by a user, produce and present on the display, a two-dimensional (2D) table comprising the one or more properties of each of the clustered data points.

2. The system according to claim 1, wherein the organ comprises a patient heart, and wherein the clustering criterion selected from a list of criteria consisting of: (i) a location of the data point in the heart, (ii) a morphology of a signal acquired at the data point, (iii) a local activation time (LAT) measured at the data point, and (iv) an anatomical feature at the data point.

3. The system according to claim 1, wherein the processor is configured to present at least the object by displaying the object over the map.

4. The system according to claim 1, wherein the processor is configured to produce and present at least the object by displaying the object in an additional 2D table.

5. The system according to claim 1, wherein the processor is configured to assign to the cluster a representative data value, which represents a calculated value corresponding to the clustered data points.

6. A method, comprising:
receiving a dataset comprising multiple data points, each data point corresponding to one or more properties of an organ of a patient;
producing, based on a clustering criterion, at least a cluster comprising two or more of the data points;

producing and presenting a map of the organ and at least an object indicative of the cluster; and in response to selection of the object by a user, producing and displaying a two-dimensional (2D) table comprising the one or more properties of each of the clustered data points.

7. The method according to claim 6, wherein the organ comprises a patient heart, and wherein the clustering criterion selected from a list of criteria consisting of: (i) a location of the data point in the heart, (ii) a morphology of a signal acquired at the data point, (iii) a local activation time (LAT) measured at the data point, and (iv) an anatomical feature at the data point.

8. The method according to claim 6, wherein presenting at least the object comprises displaying the object over the map.

9. The method according to claim 6, wherein presenting at least the object comprises displaying the object in an additional 2D table.

10. The method according to claim 6, and comprising assigning, to the cluster a representative data value, which represents a calculated value corresponding to the clustered data points.

11. A method for multi-layered visualization, the method comprising:

receiving a dataset comprising multiple data points, each data point corresponding to one or more properties of an organ of a patient;

producing a first visualization layer by clustering, based on a clustering criterion, at least a cluster comprising two or more of the data points, and displaying, an object indicative of the cluster; and producing a second visualization layer comprising a two-dimensional (2D) table having the one or more properties of each of the clustered data points, and displaying the 2D table in response to selection of the object by a user.

12. The method according to claim 11, wherein producing the first visualization layer comprises displaying the object over the map.

13. The method according to claim 11, wherein producing the first visualization layer comprises displaying the object in an additional 2D table.

14. The method according to claim 11, wherein producing the first visualization layer comprises assigning to the object a representative data value that represents a calculated value corresponding to the clustered data points.

* * * * *